(12) United States Patent
Cappello

(10) Patent No.: US 9,259,431 B2
(45) Date of Patent: Feb. 16, 2016

(54) COMPOSITIONS FOR PRODUCING SATIETY

(76) Inventor: John V. Cappello, King of Prussia, PA (US)

( * ) Notice: Subject to any disclaimer, the term of this patent is extended or adjusted under 35 U.S.C. 154(b) by 1623 days.

(21) Appl. No.: 12/710,161

(22) Filed: Feb. 22, 2010

(65) Prior Publication Data

US 2010/0151058 A1 Jun. 17, 2010

Related U.S. Application Data

(63) Continuation-in-part of application No. 11/716,339, filed on Mar. 8, 2007, now abandoned.

(60) Provisional application No. 61/288,705, filed on Dec. 21, 2009.

(51) Int. Cl.
| | | |
|---|---|---|
| *A61K 36/48* | (2006.01) | |
| *A61K 31/70* | (2006.01) | |
| *A61K 31/19* | (2006.01) | |
| *A61K 31/405* | (2006.01) | |
| *A61K 31/44* | (2006.01) | |
| *A61K 36/81* | (2006.01) | |
| *A61K 35/748* | (2015.01) | |

(52) U.S. Cl.
CPC .............. *A61K 31/70* (2013.01); *A61K 31/19* (2013.01); *A61K 31/405* (2013.01); *A61K 31/44* (2013.01); *A61K 35/748* (2013.01); *A61K 36/48* (2013.01); *A61K 36/81* (2013.01)

(58) Field of Classification Search
None
See application file for complete search history.

(56) References Cited

U.S. PATENT DOCUMENTS

| | | | | |
|---|---|---|---|---|
| 4,439,452 A | * | 3/1984 | Ehrenpreis et al. | 514/561 |
| 4,639,465 A | * | 1/1987 | Pollack et al. | 514/419 |
| 2002/0035115 A1 | * | 3/2002 | Isaacs et al. | 514/255.05 |

FOREIGN PATENT DOCUMENTS

JP 2006290792 A * 4/2005

OTHER PUBLICATIONS

Blundell, Pharmacological approaches to appetite suppression, 1991, Trends Pharma col. Sci, 12: 147-57.*

* cited by examiner

*Primary Examiner* — Terry A McKelvey
*Assistant Examiner* — Catheryne Chen
(74) *Attorney, Agent, or Firm* — Lawrence J. Shurupoff

(57) ABSTRACT

Long term weight loss can be achieved and maintained with a formulation of over-the-counter life-enhancing dietary supplements. One or more supplements stimulate the release of serotonin within the brain and one or more supplements stimulate the release of cholecystokinin into the bloodstream. The combined potentiating effect of these two mechanisms on satiety enables greater weight loss than that previously achieved by the individual mechanisms acting alone. A third weight loss mechanism can be achieved with the addition of phenylethylamine. Even more effective weight loss formulations can be achieved with the addition of a blue-green algae, such as aphanizomenon flos aqua, to provide a longer lasting weight loss mechanism.

3 Claims, No Drawings

COMPOSITIONS FOR PRODUCING SATIETY

CROSS REFERENCE TO RELATED APPLICATION

This application is a continuation-in-part application of U.S. application Ser. No. 11/716,339 filed Mar. 8, 2007, and this application also claims the benefit and priority of U.S. provisional application No. 61/288,705 filed Dec. 21, 2009.

BACKGROUND AND SUMMARY

Being overweight or obese puts one at serious risk for developing many obesity-related illnesses including heart attack, stroke, type II diabetes and hypertension. Gall bladder disease, breast cancer, prostate cancer, colon cancer, sleep apnea, osteoarthritis and respiratory problems also pose a greater risk for those who are obese.

There are numerous products available on the market, both over-the-counter ("OTC") and by prescription for controlling appetite and reducing body weight. A review of OTC products finds that many are based upon a predominance of empirical information. These OTC products typically contain caffeine, herbs of varying source and purity, and so-called fat blockers and carbohydrate blockers.

Weight control prescription formulations such as the amphetamine class can be dangerous and addictive. Newer advances of the serotonin reuptake variety and scientifically developed fat blockers are expensive and typically available only by prescription.

As detailed below, new compositions and formulations have been developed to provide a pair of weight loss mechanisms using proven weight loss technologies. This dual action approach to weight loss produces results beyond what an arithmetic summation of the individual technologies would produce. Little has been found in the literature about combining known mechanisms of weight loss, and nothing has been found using the formulations set forth below.

DETAILED DESCRIPTION OF THE EMBODIMENTS

The combined use of L-tryptophan ("tryptophan") such as in the form of 5-hydroxytryptophan ("5-HTP") to enhance serotonin production in humans and dietary supplements which stimulate cholecystokinin ("CCK") production in humans, along with additional optional ingredients has produced pronounced weight loss by creating a feeling of satisfaction, fullness and satiety for extended periods of time.

Prior uses of tryptophan are disclosed in U.S. Pat. Nos. 4,639,465 and 4,650,789, which are incorporated herein by reference in their entireties. Using the knowledge found in U.S. Pat. Nos. 4,639,465 and 4,650,789, which use tryptophan/serotonin science, a morbidly obese subject was placed on a formulation containing 100 mg of 5-HTP, 100 mg of fructose, 20 mg of niacin, and 20 mg of vitamin B6. The subject took one tablet 3 times a day, one half-hour before meals. The subject's weight loss after 4 weeks was 3 pounds. This is in line with optimal information in the literature and also in line with expectations from the prescription medications which utilize the drug Sibutramine to affect serotonin and norepinephrine.

It is also reported in the literature that long chain fatty acids, both saturated and unsaturated, are capable of stimulating the release of cholecystokinin, a factor secreted by the gall bladder which promotes the feeling of satiety. L-phenylalanine ("phenylalanine") is also known to do the same. While there are other substances which can stimulate cholecystokinin and are considered within the scope of this invention, it is believed that long chain fatty acids and L-phenylalanine are particularly beneficial.

The same morbidly obese subject was placed on a formulation provided in a capsule containing 1200 mg. of saturated and unsaturated fat derived from fish oil and borage oil. Once again, instructions were given to the subject to take the capsule three times per day, one half-hour before meals. Weight loss was recorded after 4 weeks and totaled 3 pounds. This too is in keeping with what has been reported as possible, though not always a guarantee of such weight loss.

In order to test the theory that combining these two mechanisms and technologies is superior to the arithmetic or aggregate effect of each, the same morbidly obese subject was told to take both formulations from the prior two tests at the same time, one half-hour before meals. As with the other examples, no specific diet instructions were given. Weight loss after 4 weeks in this instance totaled 18 pounds, far beyond the maximum expected by arithmetic summation of the prior two tests.

It is believed that such results beyond arithmetic aggregation can be attained in morbidly obese subjects and to some extent in other overweight individuals for several reasons. In general, weight loss subjects are known to develop tolerance to various treatments relying on a single weight loss biochemical mechanism. Because the combination of ingredients offers multiple potentiating mechanisms which produce serotonin and CCK, it may be more difficult for the individual to develop tolerance over the short or intermediate term to more than one weight loss mechanism. Likewise, these two mechanisms appear to address many eating triggers including low serotonin, depression, carbohydrate craving, obsessive disorders, anxiety and pain.

In addition, serotonin signals to the brain resulting in a sense of satiety as well as a sense of satiety in the stomach from CCK are reported from subjects taking a combination of tryptophan and a fatty acid and/or phenylalanine.

The serotonin increasing formulation as outlined above, coupled with CCK stimulating formulations containing 400 mg to 2000 mg of saturated or unsaturated fatty acid or 100 mg to 500 mg of L-phenylalinine are effective for producing weight loss in humans. This is not to exclude other dietary supplements which promote these mechanisms and which are well known to those familiar with the art.

It is also possible to include other methods of weight loss science to further expand and improve weight loss results. One example is the addition of a proteinase inhibitor such as found in potatoes, soy and beans to the dual 5-HTP and fatty acid/phenylalanine formulation described herein. This can increase the duration of satiety by prolonging the presence of CCK in the blood.

It is important to note that obesity as a disease is a chronic problem. The weight loss substances discussed herein are generally regarded as safe by the FDA and appear to have long term utility unlike many drugs which can produce toxic side effects after prolonged use. Moreover, the use of a number of different weight loss ingredients operating on different biochemical mechanisms appears to be resistant to tolerance build-up and therefore ideal for long term use.

The use of any form of tryptophan, such as 5-HTP, in combination with one or more ingredients such as a fatty acid and/or L-phenylalinine provides the basis for effective long term weight loss. The additional ingredients noted above further improve the weight loss and satiety experienced by weight loss test subjects.

Initial results suggest that the longer the combination of 5-HTP and long chain fatty acids are taken, the greater is the tendency for longer lasting endogenous regulation of appetite and maintenance of weight loss after a subject ceases taking the combination.

EXAMPLE

Forty-eight subjects with body mass indexes ("BMIs") of 30 or higher were identified. A BMI of 30 or more is categorized as obese.

These subjects were divided into 3 groups of sixteen. Each group was given the same instructions regarding exercise (daily walks of about 30 minutes) and diet (a well balanced 1200 calorie diet) to limit test variations between groups.

The first group, group A, was given a 100 mg tablet of 5-HTP available OTC under the brand "Natrol." This particular form of 5-HTP is derived from griffonia seed and comes combined with the inert ingredients of rice flour, gelatin, silicon dioxide, water and magnesium stearate. However, any brand of OTC 5-HTP can be used to increase serotonin. Subjects were told to take this tablet with a full glass of water one half-hour before meals.

The second group, group B, was given a softgel capsule of fatty acids available OTC under the brand "Multi-Oil" and available through GNC. Each capsule contains 15 calories, with 15 calories from fat. The total fat content is 1.5 grams, with zero grams of saturated fat, 0.5 grams of polyunsaturated fat and 0.5 grams of monounsaturated fat. The fat is provided as oleic acid (omega 9) at 270 mg; EPA-omega-3 (eicosapentaenoic acid) at 180 mg; DHA-omega-3 (docosahexanoic acid) at 120 mg; linolenic acid (omega-6) at 217 mg; alpha linolenic acid (omega-3) at 71 mg; and GLA-omega-6 (gamma linolenic acid) at 43 mg. Other ingredients are identified as fish body oil, gelatin, glycerin, flaxseed oil, wheat germ oil, evening primrose oil, borage oil, black currant oil, natural lemon flavor, caramel color, vitamin E, and rosemary leaf extract. The composition also contains fish, soy beans and wheat. The purpose of providing fatty acids, such as long chain fatty acids is to increase cholecystokonin secretion and release into the bloodstream. The capsule was taken with a full glass of water one half-hour before meals.

The third group, group C, was given the tablet of group A and the capsule of group B to increase both serotonin in the brain and cholecystokonin in the bloodstream. Both the tablet and capsule were taken with a full glass of water one half-hour before meals.

After 4 weeks, group A weight loss average was recorded at 3.5 pounds; group B weight loss average was recorded at 4.2 pounds, and group C weight loss average was recorded at 11.6 pounds.

It is believed that the weight loss attainable with morbidly obese subjects using the dual acting natural mechanisms of increasing serotonin and cholecystokinin was greater than the mathematical or arithmetic expectation of the summation of weight loss attributable to each individual mechanism. All of the formulations were well tolerated. A calming effect was reported by those in group A and group C.

In a post study observation, half of those subjects in group C reported no weight gain after 30 days of ceasing to use the dual acting formulation. It is believed that a longer term appetite regulation may be triggered over a period of time with regular usage of tryptophan and fatty acids.

The appetite controlling effects of 5-HTP can be enhanced by adding to the 5-HTP and fatty acid/phenylalanine formulations one or more of a sugar such as fructose, niacin, nicotinamide, pyridoxine (vitamin B6) and a salicylate such as acetylsalicylic acid (aspirin). Fructose can be added at a dosage of 250 mg, niacin and/or nicotinamide at a dosage of 25 mg, and aspirin at a dosage of 100 mg and more.

The appetite controlling effects of fatty acids and L-phenylalanine can be enhanced by adding to the 5-HTP and fatty acid/phenylalanine formulations a proteinase inhibitor such as potatoes, soy and/or beans in any suitable form such as powders and liquids.

Another improvement and enhancement to the appetite suppressing effects of L-phenylalanine is achieved with the addition of tyrosine to the formulations. The amount of L-phenylalanine that is converted to CCK can be increased with the addition of tyrosine to any formulation containing L-phenylalanine. The increased production of CCK per a given amount of L-phenylalanine results in an increase in appetite suppression.

When L-phenylalanine enters the bloodstream, it follows two different pathways and undergoes two different reactions. One reaction converts L-phenylalanine into CCK and the other reaction converts CCK into tyrosine. By providing supplemental tyrosine in any formulation with L-phenylalanine, a greater percentage of L-phenylalanine is converted to CCK and a lesser amount of L-phenylalanine is converted to tyrosine due to the presence of the supplemental tyrosine. At least 25 mg up to several hundred mg of tyrosine can be added to such formulations.

A particularly convenient form of administering a combined dosage of 5-HTP and a fatty acid is through dual encapsulation wherein 5-HTP in a solid or powder form, and fatty acid in liquid or syrup form are provided in a single capsule. Each ingredient is individually encapsulated and these capsules are further encapsulated or combined as an integral or unitary assembly which can be ingested as a single unitary dose.

This facilitates ingestion of the formulations, as they may be taken with water in a single swallow. It also ensures that both ingredients are taken, as subjects can forget to take one or the other ingredients each time before meals. This further eliminates the need for multiple pill containers.

The combined appetite suppressing effects of tryptophan and/or 5-HTP and fatty acids and/or phenylalanine can be significantly improved with the addition of phenylethylamine ("PEA"). The addition of PEA increases human metabolism as well as increases one's feeling of well being, i.e., feeling in a "good mood." This reduces excessive eating due to depression, anxiety and stress. A more effective and efficient appetite suppressing action of PEA can be achieved with the addition of a blue-green algae to any one of the formulations noted above, and particularly those algaes which include PEA. A particularly effective blue-green algae for this purpose has been found to be aphanizomenon flos aqua ("AFA"). AFA not only provides extra nutrients for promoting general health, but also functions as a natural monoamine oxidase inhibitor which increases the appetite suppressing effectiveness of PEA by slowing down the breakdown of PEA. Moreover, by adding PEA as a mood enhancer, stimulants commonly used in weight loss formulations for improving mood (such as caffeine) can be avoided.

That is, AFA includes an amino acid that reduces the human body's rate of metabolizing PEA so more PEA is converted to CCK over a longer period of time. This not only provides for a more potent appetite suppression resulting from a larger amount of CCK being produced from a given amount of PEA, but also provides for a longer duration of appetite suppression. AFA or other blue-green algaes can be used for enhancing appetite suppression in amounts ranging from about 50 mg to 500 mg. This amount can vary from between 50% less of AFA/blue-green algae to 100% more of AFA/blue-green algae.

An even more effective weight loss formulation combines L-phenylalanine, PEA, AFA, 5-HTP and, optionally, one or more of tryptophan, tyrosine, fructose, niacinamide and vitamin B6. This weight loss formulation produces three cooperative weight loss mechanisms. As noted above, L-phenylalanine, when ingested, converts to CCK to suppress appetite by producing a feeling of satiety, particularly in the gut. This is a first weight loss mechanism activated by this formulation.

A second weight loss mechanism is produced by ingesting PEA. PEA increases human metabolism so as to "burn" more calories in a given amount of time and also enhances one's mood. This boost or increase in metabolism is a second weight loss mechanism activated by this formulation. An added benefit of ingesting PEA is the production of a positive mood which helps to prevent eating caused by psychological factors other than hunger, such as "nervous eating."

The addiction of tryptophan and/or 5-HTP to the formulation provides the primary basis for a third weight loss mechanism, namely the increased production of serotonin in the brain. This increased production of serotonin results in a mental feeling of satiety and improves a person's mood and reduces the likelihood of eating triggered by undesirable moods such as depression and nervousness or stress.

A representative weight loss composition which makes a person feel satisfied and in good mental spirits by increasing serotonin, (among other means), controlling appetite with CCK production (among other means) and decreasing appetite with PEA (among other means) includes:

| | |
|---|---|
| L-phenylalanine | 250 mg |
| Phenylethylamine | 100 mg |
| Tryptophan and/or 5-HTP | 50 mg to 100 mg |
| AFA (optional) | 50 mg to 500 mg |
| Tyrosine (optional) | 50 mg |
| Fructose (optional) | 25 mg |
| Niacinamide (optional) | 15 mg |
| Vitamin B6 (optional) | 10 mg |

Each listed component in this formulation can vary between 50% less to 100% more by weight of each ingredient.

The composition listed above provides a unique combination of physiological and psychological effects and stimuli which result in an effective supplement for helping to achieve synergistic, effective and long lasting weight loss in humans. The optional addition of AFA to this formulation adds extra nutrients and serves as a natural monoamine oxidase inhibitor to increase the effectiveness of PEA.

The essential ingredients required to produce synergistic weight loss are L-phenylalanine, PEA and tryptophan and/or 5-HTP. The combination of these three (or four) ingredients has been found to produce greater weight loss than that produced by adding the individual weight losses achieved by each ingredient taken alone. This is the essential characteristic of this combination. The basis for effective weight loss is found in a combination of about 125 mg to 500 mg L-phenylalanine, 50 mg to 200 mg PEA and 25 mg 200 mg of tryptophan or 5-HTP or a combination thereof. This formulation should be taken, such as in capsule form, about one-hour before meals with at least eight ounces of water.

The effectiveness of this basic or essential combination can be marginally improved by the addition of one or more of the additional ingredients noted above. The composition can include greater amounts of each ingredient, but should include at least the minimum amounts noted above. In addition to the three essential ingredients (tryptophan and/or 5-HTP being considered one ingredient), the additional ingredients can be added as a sole additional ingredient, or in any combination of two or more additional ingredients.

It has been found that it is possible to reduce the amount of L-phenylalanine below 250 mg by adding mango or a mango extract in the amount of at least 100 mg to the formulations noted above. Mango, in the form of a juice or powder, has been found to regulate fat cells with leptin. Mango also lowers LDL and triglycerides to promote health and control appetite.

There has been disclosed heretofore the best embodiment of the disclosure presently contemplated. Obviously, numerous modifications and variations of the disclosure are possible in light of the above teachings. It is therefore to be understood that within the scope of the appended claims, the disclosure may be practiced otherwise than as specifically described herein.

What is claimed is:

1. A long lasting dietary weight loss formulation which suppresses appetite by producing a feeling of satiety in the gut, by increasing human metabolism, and by producing a mental feeling of satiety by increasing production of serotonin in the brain, comprising:

125 to 500 mg of L-phenylalanine increasing production of cholecystokinin and the release of cholecystokinin into the bloodstream to produce said feeling of satiety in the gut;

50 mg to 200 mg of phenylethylamine increasing said human metabolism and improving mood and thereby reducing excessive eating due to depression, anxiety and stress;

25 mg to 200 mg of at least one of the L-tryptophan and 5-hydroxytryptophan increasing said production of serotonin in the brain to produce said mental feeling of satiety and thereby reduce eating due to depression and nervousness;

25 mg to 1000 mg of aphanizomenon flos aqua functioning as a monoamine oxidase inhibitor increasing the appetite suppressing effectiveness of said phenylethylamine by slowing down its breakdown;

25 mg to 100 mg of tyrosine increasing the amount of said L-phenylalanine converted to said cholecystokinin and thereby increasing said feeling of satiety in the gut;

12.5 mg to 50 mg of fructose enhancing effectiveness of said at least one of L-tryptophan and 5-hydroxytryptophan;

7.5 mg to 30 mg of niacinamide enhancing effectiveness of said at least one of L-tryptophan and 5-hrydroxytryptophan; and 5 to 20 mg of vitamin B6 enhancing effectiveness of said at least one of L-tryptophan and 5-hydroxytryptophan.

2. The long lasting dietary weight loss formulation of claim 1, comprising:

250 mg of said L-phenylalanine, 100 mg of said phenylethylamine, 25 mg of said aphanizomenon flos-aqua, 50 mg of said L-tryptophan, 50 mg of said tyrosine, 25 mg of said fructose, 15 mg of said niacinamide, and 10 mg of said vitamin B6.

3. The long lasting dietary weight loss formulation of claim 1, further comprising a capsule and wherein said long lasting dietary weight loss formulation is provided in said capsule for oral ingestion.

* * * * *